(12) United States Patent
Dominguez et al.

(10) Patent No.: US 12,397,101 B2
(45) Date of Patent: Aug. 26, 2025

(54) LONG-TERM MEDICAMENT STORAGE APPARATUS AND METHODS

(71) Applicant: AMGEN INC., Thousand Oaks, CA (US)

(72) Inventors: Alan Dominguez, Thousand Oaks, CA (US); Nicholas J. Clark, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 168 days.

(21) Appl. No.: 18/027,192

(22) PCT Filed: Sep. 3, 2021

(86) PCT No.: PCT/US2021/048984
§ 371 (c)(1),
(2) Date: Mar. 20, 2023

(87) PCT Pub. No.: WO2022/081276
PCT Pub. Date: Apr. 21, 2022

(65) Prior Publication Data
US 2023/0330323 A1 Oct. 19, 2023

Related U.S. Application Data

(60) Provisional application No. 63/090,500, filed on Oct. 12, 2020.

(51) Int. Cl.
*A61M 5/00* (2006.01)

(52) U.S. Cl.
CPC ............ *A61M 5/002* (2013.01); *A61M 5/001* (2013.01); *A61M 2205/3606* (2013.01); *A61M 2209/06* (2013.01)

(58) Field of Classification Search
CPC .................. A61M 5/002; A61M 5/001; A61M 2205/3606; A61M 2209/06
(Continued)

(56) References Cited

U.S. PATENT DOCUMENTS 3,939,971 A * 2/1976 Tulis ....................... B65D 75/28
206/363
5,901,848 A * 5/1999 Gorlich .............. B65D 81/3294
206/439

(Continued)

FOREIGN PATENT DOCUMENTS

JP 2013-036986 A 2/2013
JP 2017-504438 A 2/2017
(Continued)

OTHER PUBLICATIONS

International Search Report and Written Opinion for International Patent Application No. PCT/US2021/048984, mailing date Dec. 14, 2021.
(Continued)

*Primary Examiner* — Jacob K Ackun
(74) *Attorney, Agent, or Firm* — MARSHALL, GERSTEIN & BORUN LLP; Michael P. Furmanek

(57) ABSTRACT

An apparatus for storing a medicament delivery device, the apparatus comprising: a container defining a storage cavity having an opening, the storage cavity configured to receive a syringe pre-filled with medicament; an absorbent disposed in the cavity, the absorbent at least partially hydrated with a liquid solution; and a seal member at least selectively connected with the cavity to form a seal that is at least substantially gas impermeable.

15 Claims, 11 Drawing Sheets

(58) Field of Classification Search
USPC .................................................. 206/210, 365
See application file for complete search history.

(56) References Cited

U.S. PATENT DOCUMENTS

| | | | |
|---|---|---|---|
| 5,960,956 A | 10/1999 | Langanki et al. | |
| 7,770,726 B2 * | 8/2010 | Murray | B65D 51/00 604/265 |
| 8,679,404 B2 * | 3/2014 | Liburd | A01N 1/146 206/439 |
| 2003/0168370 A1 * | 9/2003 | Merboth | A61F 2/0095 206/438 |
| 2011/0284409 A1 | 11/2011 | Murray et al. | |
| 2014/0013718 A1 * | 1/2014 | Maasarani | B65D 77/2032 206/364 |
| 2015/0014187 A1 * | 1/2015 | Gilman | A45C 11/005 206/5.1 |
| 2015/0273133 A1 * | 10/2015 | Kerschbaumer | A61M 5/3129 53/469 |
| 2015/0297861 A1 * | 10/2015 | Passalaqua | B65B 5/045 53/434 |
| 2015/0314103 A1 * | 11/2015 | Hannon | A61M 25/0009 53/431 |
| 2017/0173300 A1 * | 6/2017 | Hannon | B65D 47/141 |
| 2018/0250116 A1 | 9/2018 | Mourhatch et al. | |
| 2018/0339835 A1 | 11/2018 | Tanoguchi | |
| 2020/0054795 A1 * | 2/2020 | Farrell | A61M 25/0017 |
| 2020/0155261 A1 * | 5/2020 | O'Flynn | B65D 75/326 |
| 2022/0133426 A1 * | 5/2022 | O'Flynn | B65D 81/22 206/210 |

FOREIGN PATENT DOCUMENTS

| | | |
|---|---|---|
| WO | WO-2012/101669 A1 | 8/2012 |
| WO | WO-2013/099446 A1 | 7/2013 |
| WO | WO-2015/116257 A1 | 8/2015 |

OTHER PUBLICATIONS

Japanese Patent Application No. 2023-521549, Notice of Reasons for Refusal, dated May 27, 2025.

* cited by examiner

LONG-TERM MEDICAMENT STORAGE APPARATUS AND METHODS

CROSS-REFERENCE TO RELATED APPLICATION

This is the United States national phase of International Patent Application No. PCT/US2021/048984, filed Sep. 3, 2021, which claims priority to United States Patent Application No. U.S. 63/090,500, filed Oct. 12, 2020, the entire contents of each of which are hereby expressly incorporated herein by reference.

FIELD OF THE DISCLOSURE

The present disclosure relates to medicament storage apparatus and, more particularly, to long-term, humidity-controlled medicament storage apparatus and related methods.

BACKGROUND

Pre-filled medicament treatments can be used for home-use because the treatments can be prepared with a required, single-use dosage of a pharmaceutical product. Some pre-filled medicament treatments can include pre-filled hypodermic syringes or autoinjector products, for example. These pre-filled medicament treatments are made to be easily used by patients.

Such pre-filled medicament products can often be stored for extended periods of time, sometimes longer than two years. Although the pre-filled medicament products include various shields and seals both at the rear of the primary container and at the open needle tip, in certain environments, the medicament could potentially dry out and clog the needles of the pre-filled medicament products. When the needle clogs, the pre-filled medicament product may be more difficult to use.

SUMMARY

Disclosed herein is an apparatus for storing a medicament delivery device long term. The apparatus includes a container defining a storage cavity having an opening, the storage cavity configured to receive a syringe pre-filled with a medicament. Additionally, the container includes an absorbent disposed in the cavity, and the absorbent is at least partially hydrated with a liquid solution. The apparatus further includes a seal member at least selectively connected with the cavity to form a seal that is at least substantially gas impermeable.

Additionally disclosed herein is a method of packaging a medicament delivery device for storage. The method includes providing a container having a cavity and an opening, and disposing a syringe pre-filled with a medicament in the cavity of the container. Additionally, the method includes disposing an absorbent in the cavity of the container, the absorbent being at least partially hydrated. Further, the method describes sealing the cavity of the container with a seal member by at least selectively connecting the seal member to the cavity to form a seal that is at least substantially gas impermeable.

Additionally disclosed herein is an apparatus for storing a medicament delivery device. The apparatus includes a rigid storage container configured to receive at least one prefilled medicament delivery device or at least one container including a prefilled medicament delivery device. The apparatus also includes an absorbent carrier disposed in the rigid storage container, the absorbent carrier including an absorbent at least partially hydrated with a liquid solution.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings are necessarily to scale.

FIG. 8b is an additional view of a graphical display disposed on the rigid storage container of FIG. 8a.

FIG. 8c is an additional view of a graphical display disposed on the rigid storage container of FIG. 8a.

FIG. 8d is a fingerprint lock interface disposed on the rigid storage container of FIG. 8a.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Pre-filled medicament delivery devices are provided to patients for their personal administration at home, for example. Even when stored under ideal conditions, the pre-filled medicament delivery device can dry out and become clogged. When the medicament in the pre-filled medicament delivery device is dried or clogged, it may be difficult or painful to administer the medicament in the pre-filled medicament delivery device.

The apparatus for storing medicament delivery devices of the present disclosure inhibits the drying out of medicament during long-term storage. For example, the apparatus may include an absorbent designed to maintain an elevated relative humidity in an enclosed container. The absorbent is any material that can be hydrated, store moisture, and release the moisture to maintain a humid environment in an enclosed area. Additionally, the absorbent can be optimally designed based on the size of the container, a desired relative humidity level, and the length of storage, etc.

Additionally, the apparatus and method of using the apparatus can include sterilizing the apparatus for storing medicament delivery devices, including a container, the medicament delivery device, and the absorbent. For example, the apparatus can be sterilized using a sterilant such as a vapor pressure hydrogen peroxide (VPHP, also referred to as vaporized hydrogen peroxide (VHP)) process and/or hydrate the absorbent in a water sterilants solution, such as an ethanol, isopropanol, or benzyl alcohol solution. As a result, the apparatus for storing the medicament delivery device can be sterile and safe for personal use when the patient opens the apparatus for storing medicament delivery devices to self-administer a medicament.

Figure 1:
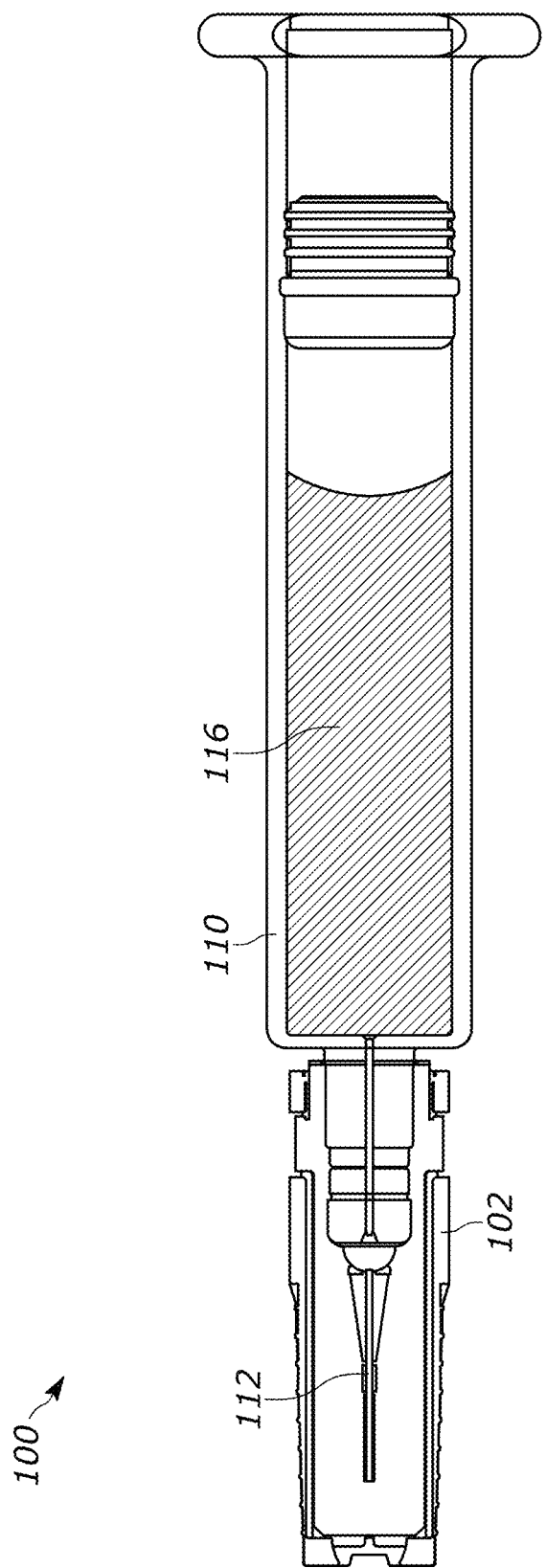
FIG. 1 is a side view of a pre-filled hypodermic syringe including a needle shield.

FIG. 1 is a side view of a pre-filled hypodermic syringe 100 including a needle shield 102. The pre-filled hypodermic syringe 100 includes a container 110 in fluid communication with a needle 112. The needle shield 102 covers the needle 112 and protects the needle 112 from an exterior environment. The sealed container 110 is filled with a dosage of medicament 116. The container 110 is filled with a predetermined amount of medicament 116, that, for example, is suitable for convenient personal use by patients. As shown in FIG. 1, the pre-filled hypodermic syringe 100 and the needle shield 102 are transparent, however, in other examples, the pre-filled hypodermic syringe 100 and/or the needle shield 102 is opaque.

The needle 112 is in fluid communication with the container 110 and an exterior environment. The needle 112 is disposed within the needle shield 102. The needle shield 102 can be composed of plastic, rubber, silicone or similar material capable of protecting the needle 112 during transportation and storage and covering the needle 112 from the surrounding environment to ensure the needle 112 is sterile. In some examples, the needle shield 102 can be nonporous material to completely seal the needle 112 from the surrounding environment or the needle shield 102 can be a porous material that partially seals the needle 112 from the surrounding environment, because the needle shield 102 is gas permeable.

The medicament 116 may be subject to drying out and can be more difficult to use. For example, the needle shield 102 is porous enough to allow moisture from the medicament to evaporate. As a result, medicament 116 that may reside in the needle 112 can at least partly solidify, and, can partially or entirely clog the needle. When the needle is partially clogged in a hypodermic syringe, the syringe plunger may be difficult and painful to actuate. For example, a syringe plunger is difficult to use if actuating the plunger requires approximately 40 Newtons (N) of force or more.

Similarly, medicament 116 can be stored and dry out in an autoinjector product, such as an autoinjector cartridge. As a result, the medicament 116 can still dry out and clog a needle carried by the autoinjector cartridge. Accordingly, an autoinjector needle can become partially or entirely clogged. When the needle is partially or entirely clogged, the autoinjector may, when initiating a medicament delivery, provide an error message that the force required to deliver the medicament 116 exceeded a preset threshold. For example, autoinjectors are designed to delivery between 20 and 120 Newtons (N) of force.

Figure 2:
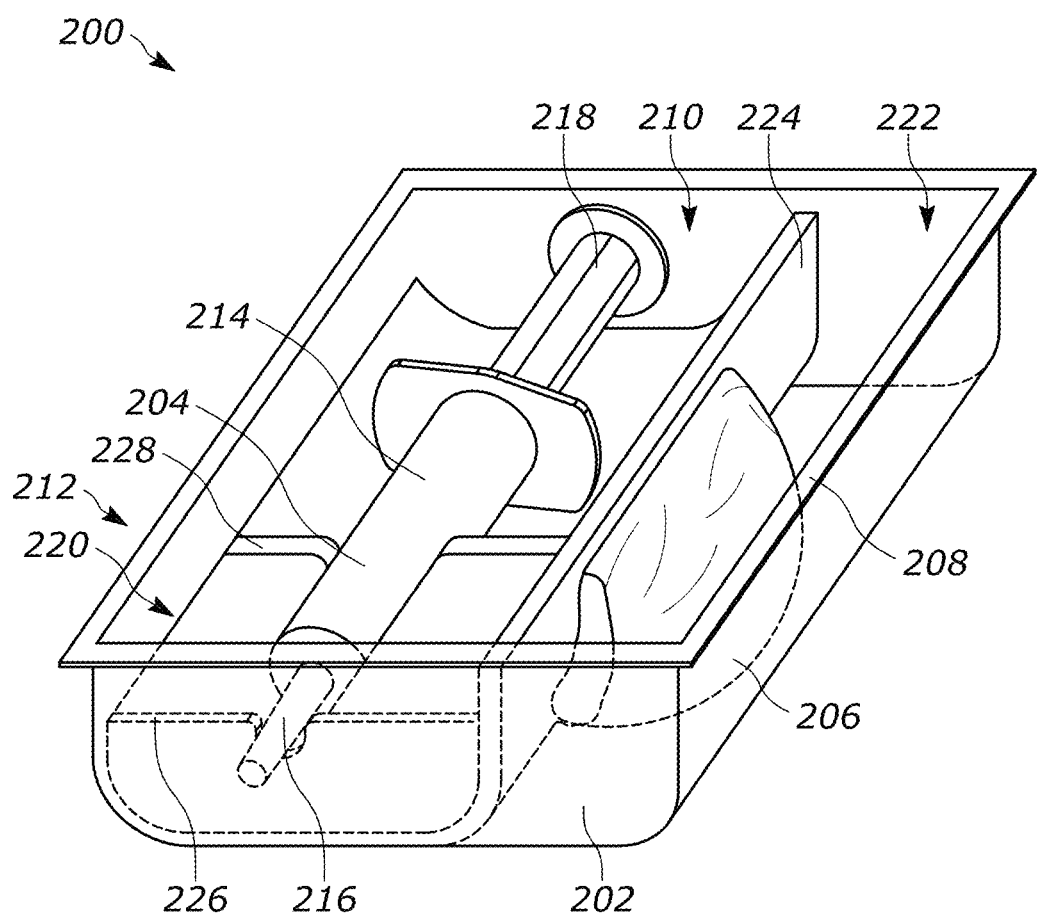
FIG. 2 is a perspective view of a container for storing a medicament delivery device in accordance with the present disclosure, such as the pre-filled hypodermic needle of FIG. 1.

FIG. 2 illustrates an embodiment of the medicament storage apparatus 200. FIG. 2 provides a perspective view of the apparatus 200 including a container 202 for storing a medicament delivery device 204, such as the pre-filled hypodermic needle 100 of FIG. 1. As shown in FIG. 2, the apparatus additionally includes an absorbent 206 in the container 202. The container 202 provides long-term protection and storage for the medicament delivery device 204.

The container 202 includes a container edge 208 circumscribing an opening 210 and a storage cavity 212. The storage cavity 212 is configured to receive the medicament delivery device 204, such as a syringe 214 pre-filled with medicament. The syringe 214 additionally includes a needle shield 216 and a syringe plunger 218, similar to the pre-filled hypodermic syringe 100 of FIG. 1. As shown in FIG. 2, the container 202 is transparent, however the container 202 can be translucent, cloudy, or opaque. For long-term storage, the container 202 is preferably made of a rigid, gas impermeable material, such as plastic, to seal the environment within the container 202 and protect the syringe 214 from damage during transportation and storage.

The absorbent 206 is also disposed in the storage cavity 212 of the container 202. The absorbent 206 is at least partially hydrated with a liquid solution, such as a water solution. Alternatively, the liquid solution can be a water and alcohol solution to maintain the sterility of the container 202 during long-term storage. The absorbent 206 can be a humidification pouch, a humidor bag, a sponge, a fabric article, liquid gels, or similar liquid absorbent material that also allows the liquid to evaporate over time. Depending on the desired humidity in the container 202 and the absorbent 206 material, the absorbent may be soaked in the liquid solution for a predetermined period of time (e.g., 1 second, 5 seconds, 10 seconds, 20 seconds, etc.). Alternatively, the absorbent may be provided a specified volume of liquid solution (e.g., 0.5 milliliter (mL), 1 mL, 2 mL, 5 mL) or a specified weight of liquid solution (e.g., 0.5 grams (g), 1 g, 2 g, 5 g). Furthermore, in some examples, the absorbent may be provided liquid solution proportional to the dry weight of the absorbent (e.g., 50 percent (%) dry weight of liquid solution, 100%, 150%). Accordingly, any method of measuring an amount of liquid absorbed by the absorbent could be considered within the scope of the disclosure.

The storage cavity 212 and its contents are sterile, including the absorbent 206 and syringe 214. Before and/or after placing the syringe 214 and the absorbent 206 in the container 202, the storage cavity 212 may additionally undergo a sterilization process. Sterilizing the storage cavity 212 and the syringe 214 may include exposing the storage cavity 212 and the syringe 214 to a sterilant. For example, the container and its contents can undergo a vapor phase hydrogen peroxide (VPHP) 5 sterilizing process, however other medical storage sterilization methods are also considered within the scope of the disclosure.

The storage cavity 212 of the container 202 is divided into a first sub-cavity 220 and a second sub-cavity 222 separated by a container wall 224, the first sub-cavity 220 containing the syringe 214 and the second sub-cavity 222 containing the absorbent 206. In other examples, the storage cavity 220 could include additional container walls to divide the storage cavity 220 into more than two sub-cavities. While the absorbent 206 is shown in the second sub-cavity 222, the absorbent can be disposed in the first sub-cavity 220 along with the syringe 214. The first sub-cavity includes a first retainer 226 and a second retainer 228 that receive the syringe 214. The first retainer 226 and the second retainer 228 can additionally secure the syringe 214 and inhibit or reduce movement of the syringe 214 within the first sub-cavity 220.

Figure 3:
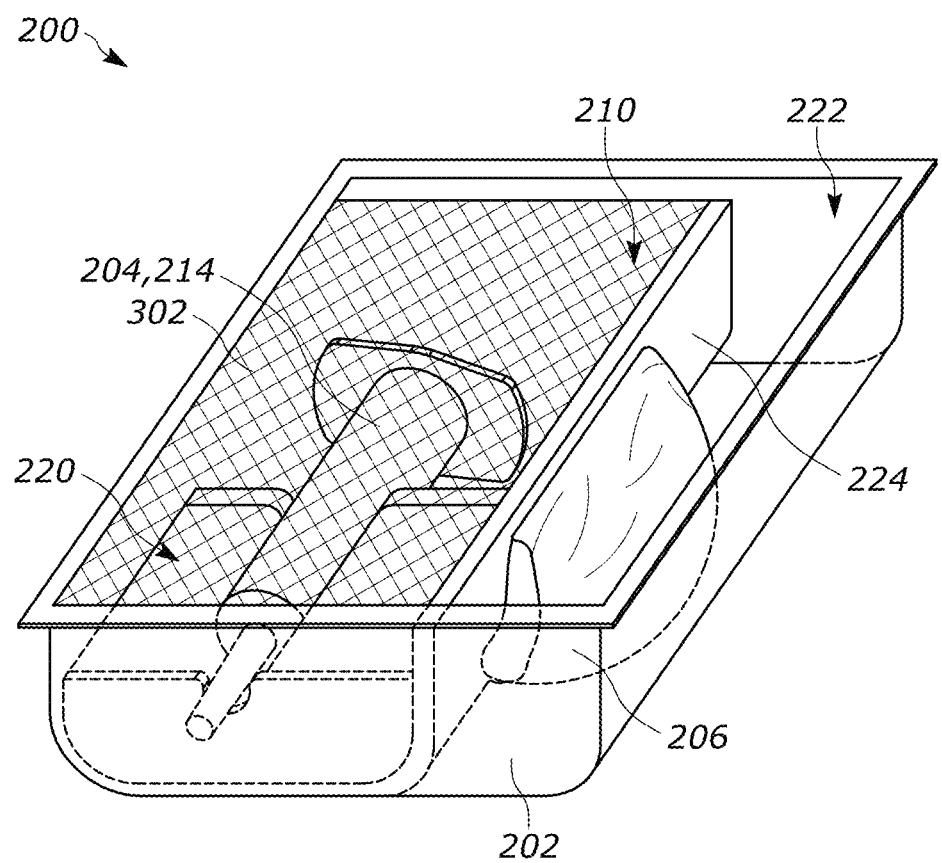
FIG. 3 is a perspective view of the container for storing a medicament delivery device of FIG. 2, further including a gas permeable seal member disposed over a first sub-cavity.

FIG. 3 is a perspective view of the container 202 for storing a medicament delivery device 204 of FIG. 2, further including a gas permeable seal member 302 disposed over the first sub-cavity 220. Gases and vapors can pass through the gas permeable seal member 302. But the gas permeable seal member 302 prevents larger particles and materials from passing into or out of the first sub-cavity 220, including bacteria and fungus spores. Gas permeable seal member 302 can include any of a variety of gas permeable seal members well known in the field of sterile medical packaging.

As shown in FIG. 3, the gas permeable seal member 302 is disposed on the container 202 over at least part of the opening 210 enclosing at least part of the first sub-cavity 220 containing the syringe 214. The gas permeable seal member 302 allows gas and vapor to pass through, but protects the syringe 214 from bacteria, mold, and other particulates. Thus, the gas permeable seal member 302 maintains the sterility of the syringe 214 for long-term storage. In some embodiments, the gas-permeable seal member 302 can additionally cover the second sub-cavity 222.

As shown in FIG. 3, the absorbent 206 is disposed in the second sub-cavity 222, outside the gas permeable seal member 302. Even though the first sub-cavity 220 is covered by the gas permeable seal member 302, moisture that evaporates from the absorbent 206 can fill the entire container. Because the gas permeable seal member is permeable to water vapor, moisture from the absorbent 206 fills the entire cavity, including the first sub-cavity 220.

Figure 4:
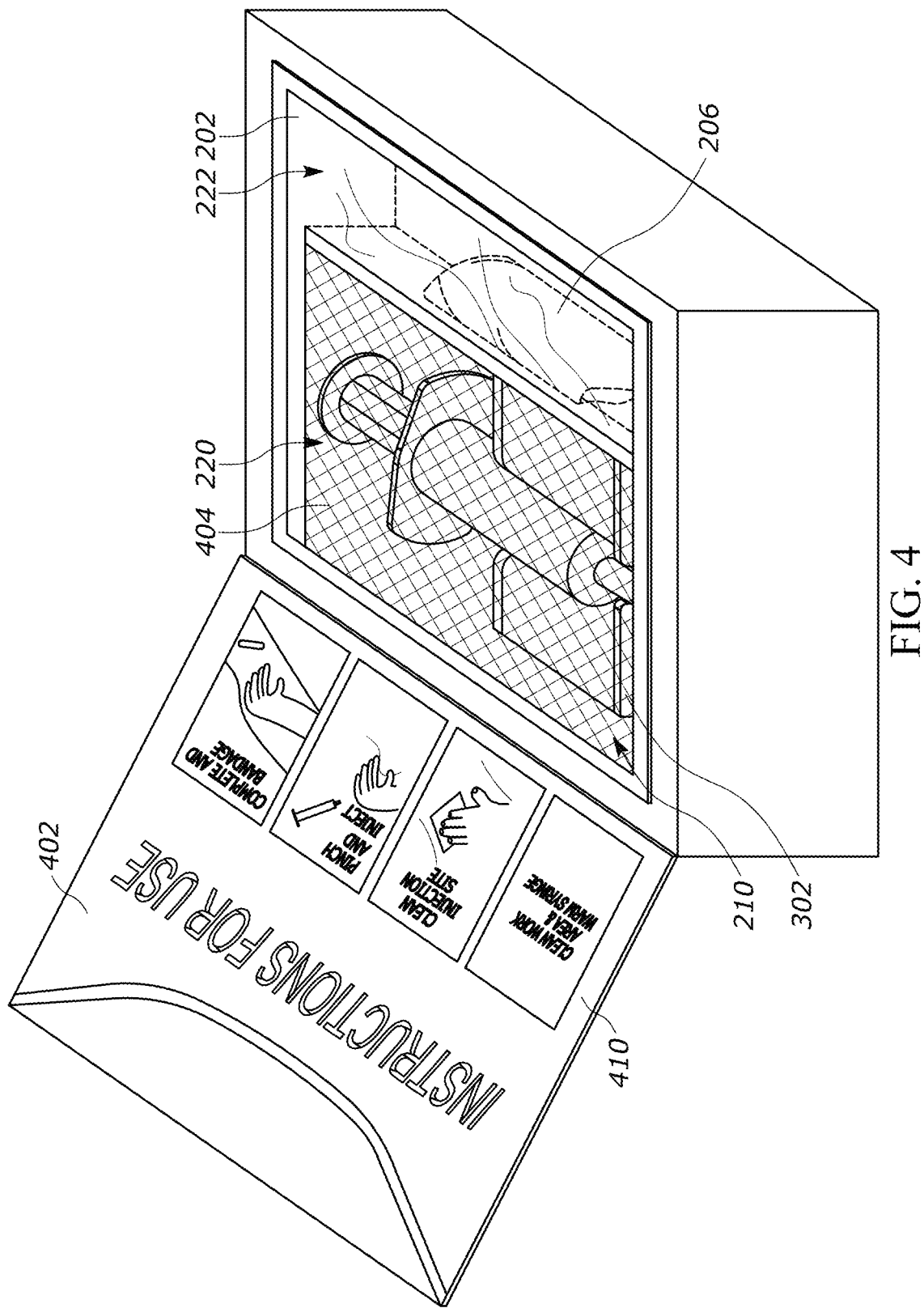
FIG. 4 is a perspective view of the container for storing a medicament delivery device of FIG. 3, further including a member disposed over the container.

FIG. 4 is a perspective view of the container 202 for storing a medicament delivery device 204 of FIGS. 2 and 3, further including packaging 402 and a seal member 404, which in some versions can be a gas impermeable seal member, disposed over the container 202. The packaging 402 including the container 202 is configured for long-term storage, sometimes in excess of two years. Additionally, the packaging 402 can include instructions for use 410 or other information useful to the end user or patient.

The seal member 404 is disposed adjacent the container 202 and over the opening 210 to enclose the entire storage cavity 212. Accordingly, the gas permeable seal member 302 is between the seal member 404 and the container 202. The seal member 404 forms a gas impermeable seal between the seal member 404 and the container 202. As a result, the container 202 is an enclosed environment, and the sterility of the container 202 is maintained as long as the seal is maintained.

The absorbent 206 is hydrated and disposed in the second sub-cavity 222 before the seal member 404 is disposed on the container. The absorbent 206 releases moisture to maintain the humidity within the sealed container 202 at a desired level. As a result, if the container is maintained at a high relative humidity, medicine in the medicament delivery device 204 will not dry out nor get clogged. The absorbent 206, disposed in the second sub-cavity, maintains a high relative humidity (e.g., greater than 60% relative humidity) throughout the entire container 202. For example, the relative humidity can be maintained above 75% relative humidity for extended periods of time (e.g., 1 month, 6 months, 1 year, 3 years). Thus, the absorbent 206, releasing maintaining humidity in the container, can inhibit clogging of the medicament delivery device 204 for months or years.

Figure 5:
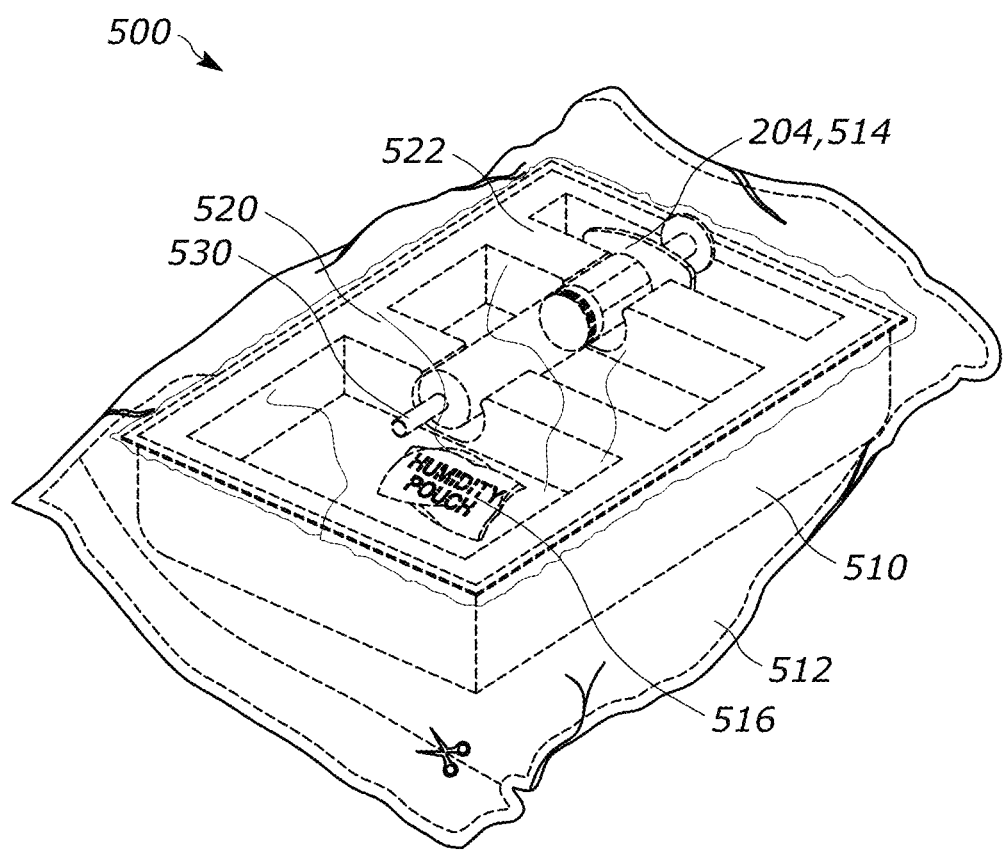
FIG. 5 is a perspective view of an alternative apparatus for storing a medicament delivery device in accordance with the present disclosure.

FIG. 5 illustrates an additional embodiment of a medicament storage apparatus. FIG. 5 provides a perspective view of an alternative apparatus 500 for storing the medicament delivery device 204. In contrast to the apparatus 200 of FIGS. 2, 3, and 4, the apparatus 500 of FIG. 5 includes a container 510 disposed in a sealed gas-impermeable bag 512. The gas-impermeable seal member is a sealed gas-impermeable bag 512 in which the container 510, the syringe 514, and the absorbent 516 are disposed.

The container 510 is constructed from a rigid material, capable of protecting the medicament delivery device 204, such as a syringe 514, during storage and transportation. Additionally, the container 510 includes a first retainer 520 and a second retainer 522. The first retainer 520 and the second retainer 522 receive, and in some examples, secure the syringe 514 from movement within the container 510. Additionally, the container 510 can include a seal member 534 that can be either gas permeable or gas impermeable. As a result, the absorbent 516 may maintain the humidity of the entire gas-impermeable bag 512 or just the container 510.

Additionally, the container is placed within the gas-impermeable bag 512. The gas-impermeable bag 512 is sealed to maintain a sterile environment including the container 510. The gas-impermeable bag 512 may undergo a sterilization procedure (e.g., the VPHP process) while the container 510 is disposed in the gas-impermeable bag 512. After being sealed, the gas-impermeable bag 512 needs to be cut or torn open to remove the container 510. In some preferred embodiments, the gas-impermeable bag 512 is designed to be cut for arthritic patients that may not prefer tearing the gas-impermeable bag 512 open.

As shown in FIG. 5, the absorbent 516 is disposed near a needle shield 530 of the syringe 516, but can be disposed anywhere within the container 510. The absorbent 516, disposed in the container 510, maintains a high relative humidity (e.g., greater than 60% relative humidity) throughout the entire container 510. Accordingly, the absorbent 516, disposed in the container 510, can inhibit the clogging of a medicament delivery device, such as the syringe 514.

Figure 6:
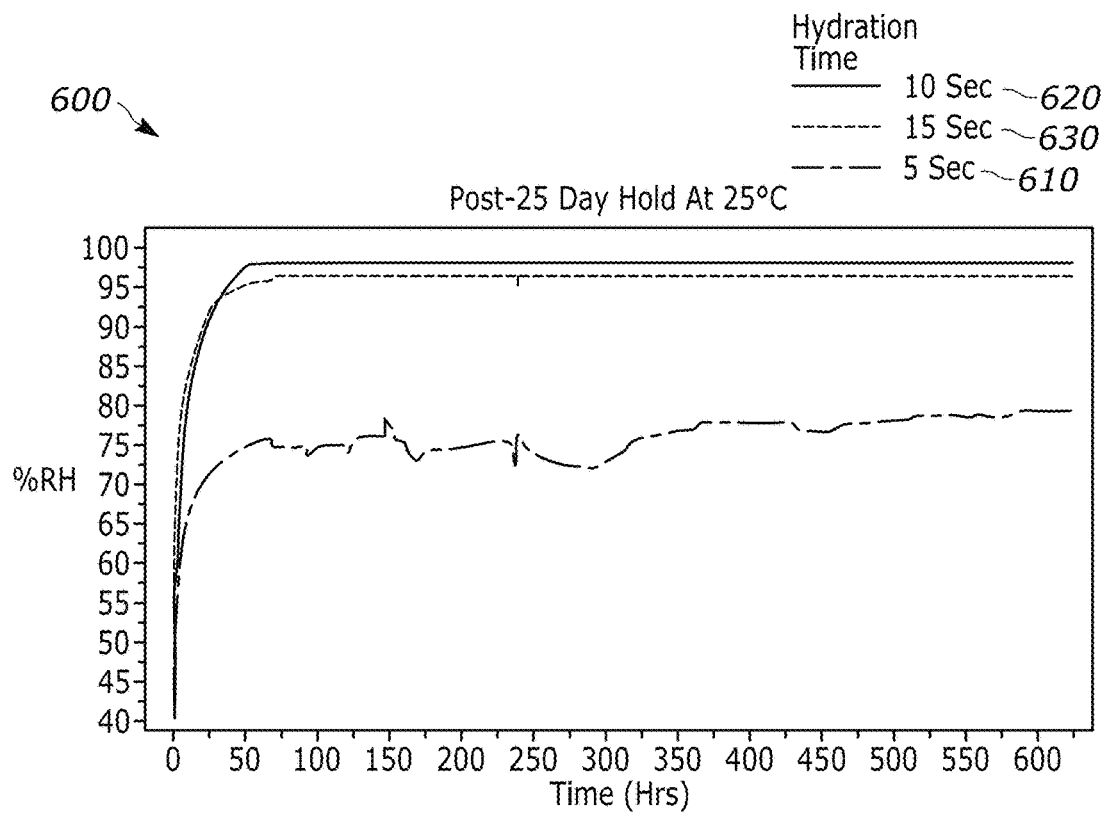
FIG. 6 is an example graph of relative humidity in an enclosed container based on a hydration time for an absorbent.

FIG. 6 is an example graph 600 of relative humidity in an enclosed container based on a hydration time for an absorbent. The horizontal axis relates to a time in hours from zero (0) hours to 625 hours (approximately 26 days). Additionally, the vertical axis relates to measurements of relative humidity in the enclosed container from 40% to 100% relative humidity. The graph 600 incudes a first dataset 610, a second dataset 620, and a third dataset 630 that measure the relative humidity in the enclosed container over time.

As shown in FIG. 6, the first dataset 610 corresponds to the relative humidity for an absorbent hydrated for 5 seconds. The first dataset 610 shows humidity fluctuating between 70% and 80%. In contrast, the second dataset 620 (corresponding to 10 seconds of hydration) and the third dataset 630 (corresponding to 15 seconds of hydration) both keep the container at a relative humidity between 95% and 100%. Accordingly, hydration time can be used to control the relative humidity in the container over extended periods of time.

Although each dataset of graph 600 is measured in hydration time, the datasets could be measured in weight, volume, or other measurement of stored liquid. For example, for some absorbents, 5 seconds of hydration (corresponding to the first dataset 610) could equal approximately 6 grams (g) of water or approximately 6 milliliters (mL) of water while 15 seconds of hydration (corresponding to the third dataset 630) could equal approximately 9 g of water or 9 mL of water. Additionally, hydration for 10 minutes could only absorb 16 g (or 16 mL) of water. Other absorbents may absorb a weight or volume of water faster or slower.

The absorbent can be hydrated for a preset period of time based on design considerations, including the size of the container, the desired relative humidity, and the permeability of the needle shield covering the needle. Typically, the absorbent is hydrated for a period of time between approximately 5 seconds and approximately 10 seconds to maintain a relative humidity between 75% and 95%. As indicated by the first dataset 610, the absorbent maintained a relative humidity between 70% and 80% for the duration of the experiment. Accordingly, longer hydration time would result in a higher relative humidity maintained in the container.

Absorbents of different designs may require more or less hydration time to maintain a similar relative humidity. Additionally, absorbents placed in larger containers may require more hydration than similar absorbents placed in smaller containers. Furthermore, if the medicament delivery device includes a nonporous needle shield, the relative humidity does not need to be as high if the needle shield were more porous, because the nonporous needle shield inhibits the drying of the medicament. Each of the above factors can be considered when designing the apparatus of the present disclosure.

Figure 7:
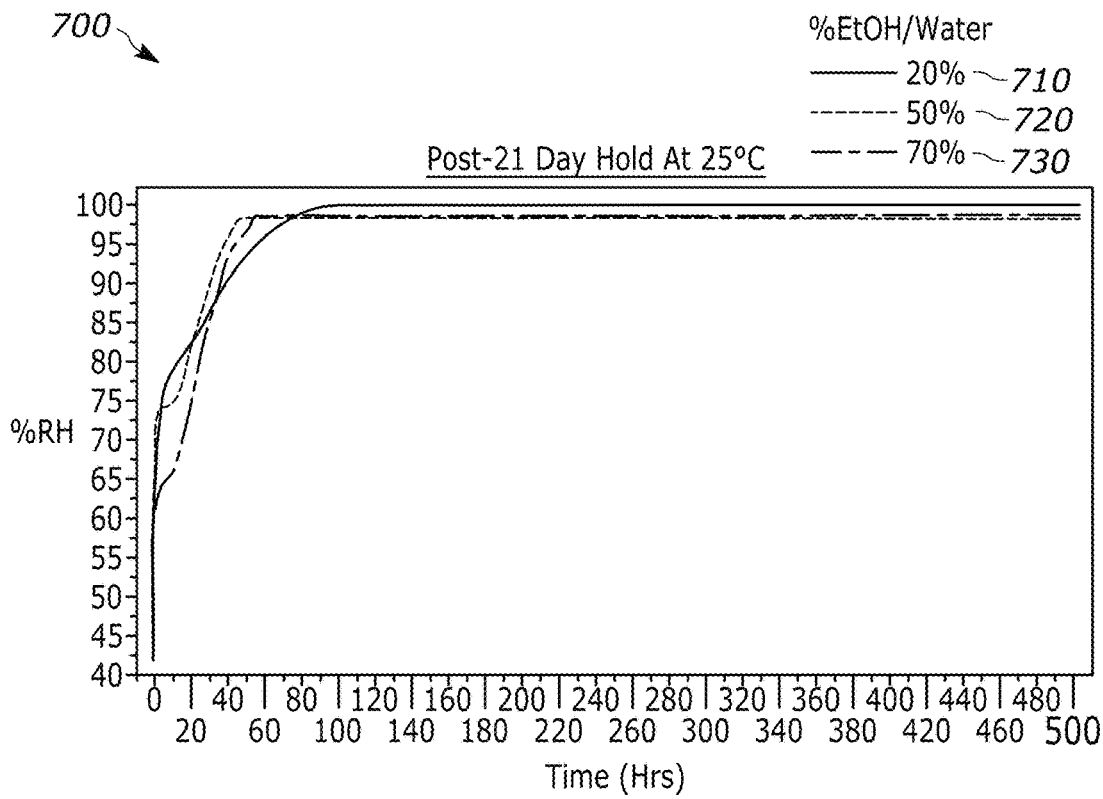
FIG. 7 is an example graph of relative humidity in an enclosed container based on hydration of an absorbent with a water and alcohol solution.

FIG. 7 is an example graph 700 of relative humidity in an enclosed container based on hydration of an absorbent with a water and alcohol solution (i.e., ethanol alcohol). The horizontal axis relates to a time in hours from zero (0) hours to 520 hours (approximately 21 days) of measuring the relative humidity in the container. Additionally, the vertical axis relates to measurements of relative humidity in the enclosed container from 40% to 100% relative humidity. The absorbent can by hydrated with other liquid solutions other than water or water and ethanol alcohol, such as benzyl alcohol or other sterilants.

As shown in FIG. 7, an absorbent is hydrated in an ethanol water solution (EtOH) for 15 seconds. Ethanol is often used in antibacterial applications, and could be added to the hydration solution to further maintain the sterile environment of the container during long-term storage. Similar chemicals could be added to the hydration solution to maintain a desired relative humidity and a sterile environment in the container, such as isopropanol or benzyl alcohol solutions. The percentage of ethanol in the ethanol-water solution appears to provide minimal effect on the relative humidity maintained in the container.

As shown in FIG. 7, the first dataset 710 corresponds to an absorbent soaked in a 20% EtOH solution for 15 seconds. The second dataset 720 corresponds to an absorbent soaked in a 50% EtOH solution for 15 seconds. And the third dataset 730 corresponds to an absorbent soaked in a 70% EtOH solution for 15 seconds. As shown in FIG. 7, each of the first dataset 710, the second dataset 720, and the third dataset 730 show the humidity in the container is maintained above 95%. Thus, the graph 700 indicates the percent of ethanol in the EtOH solution has little effect on the humidity maintained in the container.

Although each dataset of graph 700 is measured in hydration time, the datasets could be measured in weight, volume, or other measurement of stored liquid. For example, for some absorbents, 15 seconds of hydration could equal approximately 1.5 grams (g) of EtOH or approximately 1.6 milliliters (mL) of EtOH solution. Similarly, hydration for 10 minutes might only equal approximately 2 g of EtOH or 2.2 mL of EtOH. Other absorbents may absorb a weight or volume of water faster or slower.

Figure 8A:
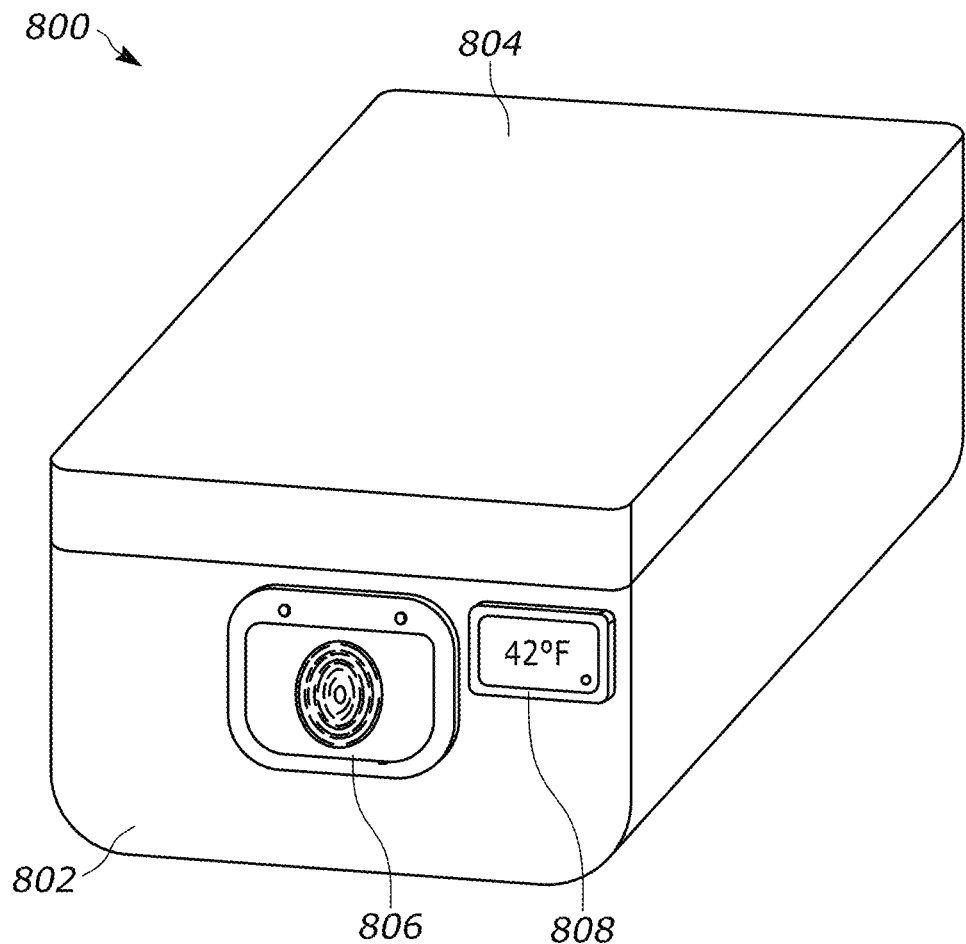
FIG. 8a is a perspective view of a rigid storage container in accordance with the present disclosure.

FIG. 8*a* is a perspective view of a rigid storage container 800 made in accordance with the present disclosure. The rigid storage container 800 is a container made of a rigid material and includes a storage cavity. The rigid container 800 includes a bottom 802 and a top 804. Both the bottom 802 and the top 804 fully enclose the rigid storage container 800. The rigid storage container 800 can be made of a rigid plastic, metal, or similar material that can support the weight of the rigid storage container 800 and protect the contents of the rigid storage container 800. In some examples, the rigid storage container 800 can additionally include a handle for easier carrying of the rigid storage container 800.

The rigid storage container 800 is preferably designed to be a sleek and slim space saving design, so as to minimize the amount of space the rigid storage container uses in a patients refrigerator. Additionally, the outer casing of the rigid storage container 800 is made of a durable plastic or a stainless steel that can have antimicrobial properties. Other materials are possible. The casing may also be of a double-walled construction to improve the insulation properties of the rigid storage container 800. However, in the event of power failure or extended storage outside of a refrigerator, the rigid storage container 800 may include a coolant or alcohol filled compartment (not shown). The coolant or alcohol compartment passively cools the rigid storage container 800 via the coolant or alcohol filled compartment. Thus, the rigid storage container 800 can, for short durations, be cooled if the temperature within the rigid storage container is rising above preset thresholds. Alternatively, the rigid storage container 800 includes battery powered apparatus, including the coolant or alcohol filled compartment, to allow for battery powered cooling of the rigid storage container 800.

The rigid storage container 800 includes a locking mechanism 806 and a graphical display 808. Both the locking mechanism 806 and the graphical display 808 are powered by batteries (not shown) stored within the rigid storage container 800. In other examples, the rigid storage container 800 could be powered via an alternative electrical sourced, including being plugged into an electrical outlet or having a photovoltaic cell in addition to batteries. As shown in FIG. 8*a*, the locking mechanism 806 and the graphical display 808 are disposed on a sidewall of the bottom 802. In other examples, the locking mechanism 806 and/or the graphical display 808 are disposed on the top 804 or elsewhere on the bottom 802. The graphical display 808, as shown, displays a temperature value corresponding to the temperature of the interior of the rigid storage container 800. Alternatively, the graphical display 808 can display a humidity corresponding to the relative humidity of the interior of the rigid storage container 800. As such, the container 800 can include a temperature sensor and/or a humidity sensor (not shown) disposed inside of the container and communicatively coupled to the graphical display 808. Other sensors can also be included.

Figure 8B:
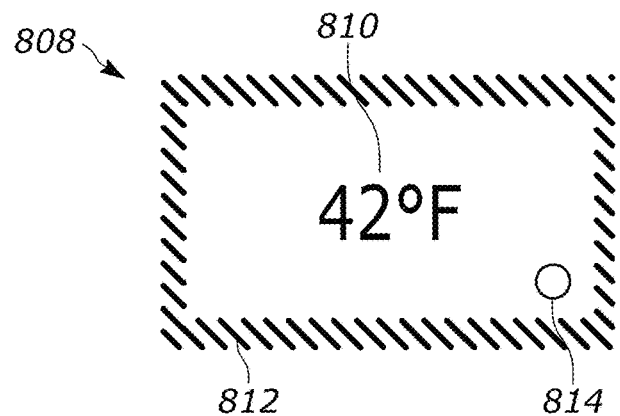

FIG. 8b is an additional view of the graphical display 808 disposed on the rigid storage container 800 of FIG. 8a. The graphical display 808 includes a first display 810. As shown in FIG. 8b, the first display 810 additionally includes a graphic indicating a temperature within the rigid storage container 800 of FIG. 8a. The example first display 810 shows the internal temperature of the rigid storage container 800 is now 44 degrees Fahrenheit (° F.). The graphical display 808 additionally includes a color indicator 812. The color indicator 812 corresponds to the information provided on the first display 810. For example, the color indicator 812 can display a color indicating a positive condition, such as green to indicate the temperature is within an appropriate or target range of temperatures. Additionally, the graphical display 808 includes a display toggle 814. The display toggle 814 can be pressed to activate the graphical display 808 or alternate the graphical display between temperature, humidity, remaining battery life, or hours until temperature excursion. Drug and medicament are designed to be stored within a set range of storage temperatures. Temperature excursion is when the medicament or drug in the drug delivery device is exposed to temperatures outside the range of storage temperatures for the drug or medicament. In some examples, the graphical display 808 can include more or fewer display toggles 814 than shown in FIG. 8b.

Figure 8C:
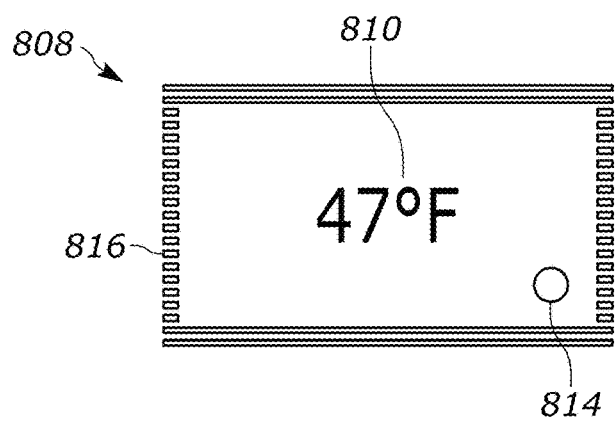

FIG. 8c is an additional view of the graphical display 808 disposed on the rigid storage container 800 of FIG. 8a. The graphical display 808 of FIG. 8c includes a second display 812, different from the first display 810 of FIG. 8b. As shown in FIG. 8c, the interior temperature of the rigid storage container 800 is now 47 degrees Fahrenheit (° F.) and the color indicator 812 has changed to a second color. For example, the color indicator 812 can transition from green associated with appropriate or target range (i.e., 44° F.) to red associated with the higher 47° F., which is outside of the appropriate or target range. In other examples, the color indicator 812 can change based on an internal relative humidity, an amount of remaining battery life, or hours until temperature excursion.

Figure 8D:
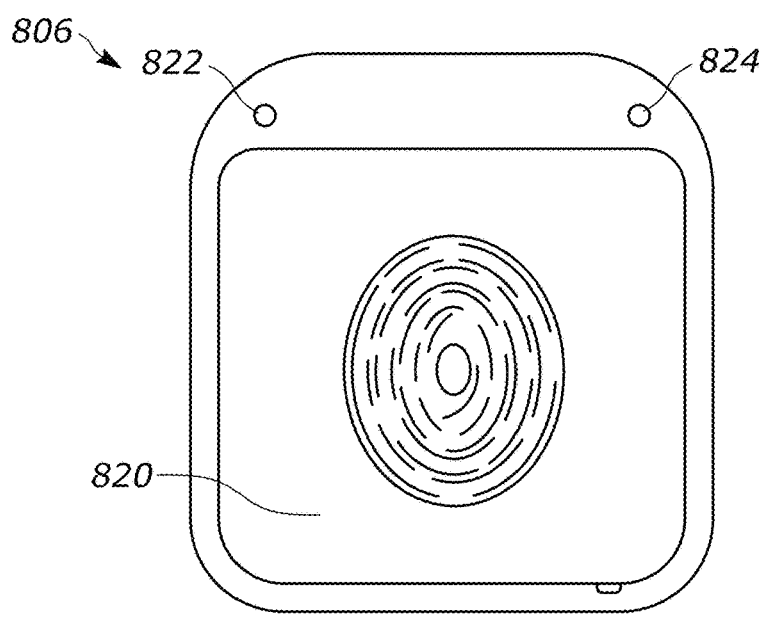

FIG. 8d is a fingerprint lock interface 806 disposed on the rigid storage container 800 of FIG. 8a. The fingerprint lock interface 806 inhibits tampering with the contents of the rigid storage container 800. The fingerprint lock interface 806 recognizes a fingerprint of a patient or other authorized user and unlocks the rigid storage container 800. The fingerprint lock interface 806 includes a fingerprint reader 820 and a first toggle 822 and a second toggle 824. The fingerprint reader 820 scans a fingerprint placed on the fingerprint reader 820 and verifies if the fingerprint matches the fingerprint of the patient or other authorized user. Additionally, if needed, the first toggle 822 and the second toggle 824 can be used to control the fingerprint lock interface 806.

In other embodiments the fingerprint lock interface 806 could be a number pad for entering a numerical pin or a key hole for use with a key, or any similar locking mechanism. Additionally, the rigid storage container 800 can include two or more locking mechanisms. For example, a mechanical locking mechanism could be used if the batteries in the rigid storage container 800 cannot effectively power the fingerprint lock interface 806.

Figure 9:
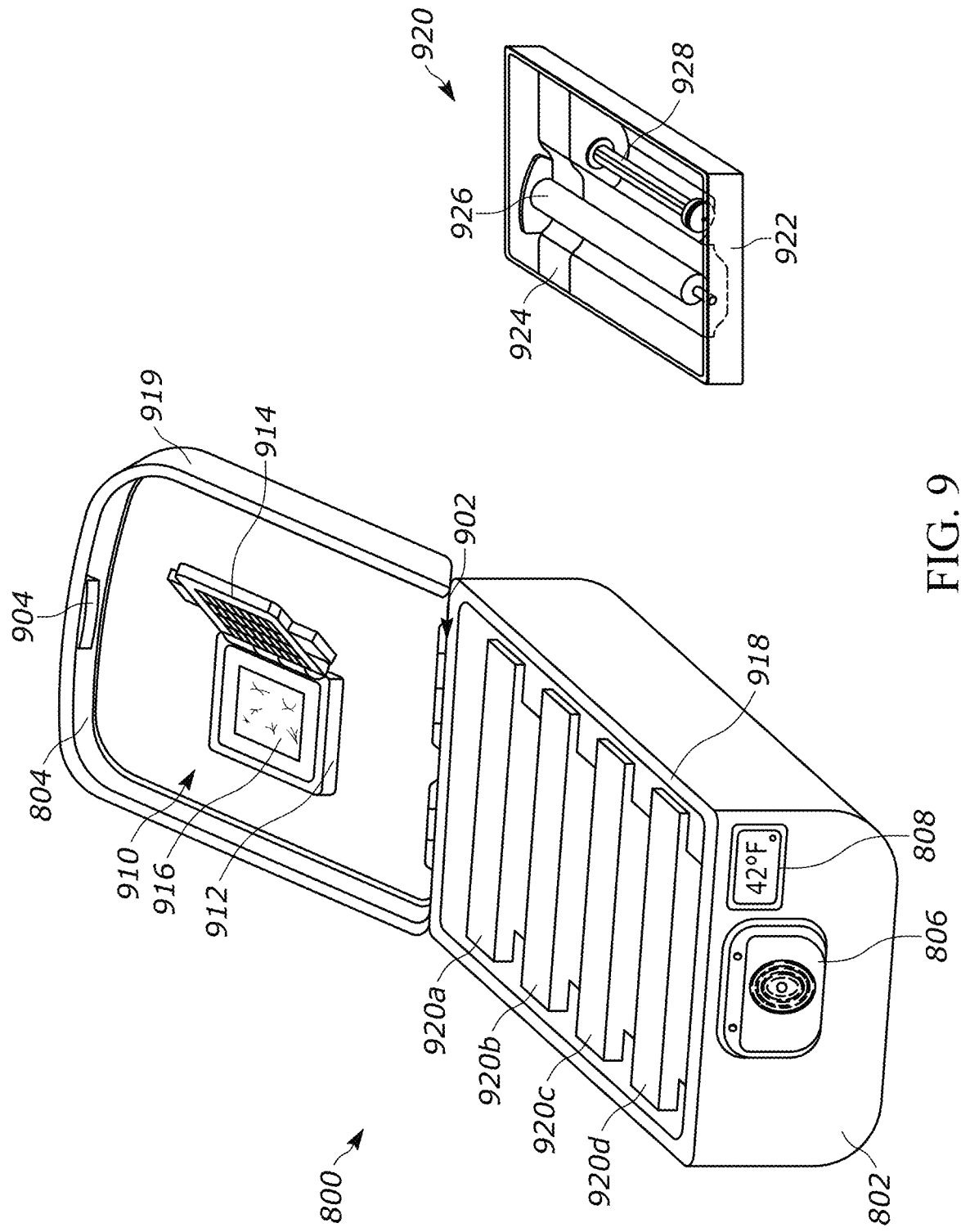
FIG. 9 is a perspective view of the rigid storage container of FIG. 8a in an open state for storing at least one container for storing a medicament delivery device.

FIG. 9 is a perspective view of the rigid storage container 800 of FIG. 8a in an open state. As shown in FIG. 9, the rigid storage container 800 opens along hinges 902 to show the storage cavity of the rigid storage container 800. The top 804 of the rigid storage container 800 additionally includes a latch 904. The latch 904 engages with the fingerprint lock interface 806 to secure the top 804 in a closed position. When the top 804 is in the closed position and the latch 904 is engaged with the fingerprint lock interface 806, the rigid storage container 800 forms a sealed interior container.

The rigid storage container 800 additionally includes an absorbent carrier 910. The absorbent carrier 910 includes a base 912 and a gas permeable lid 914. The gas permeable lid 914 allows moisture stored in an absorbent 916 to pass therethrough. The absorbent 916 is similar to the absorbent 206. For example, the absorbent 916 can absorb similar water solutions as absorbent 206 and can be made of similar materials as absorbent 206. The gas permeable lid 914 can be opened so the absorbent 916 can be removed and rehydrated or replaced, for example, by the patient or other end user. In some examples, the absorbent 916 is antimicrobial to impede microbe growth during storage. The rigid storage container 800 further includes edge 918, for enclosing the inner container of the rigid storage container 800 from the exterior environment. In some examples, the edge 918 closes against an inner surface of the top 804 or an edge 919 of the top 804. Additionally the edge 918 and/or the edge 919 may include an elastic material to seal the container 800 from the exterior environment.

The rigid storage container 800 is designed for storing at least one container 920 for storing a medicament delivery device. As shown in FIG. 9, the rigid storage container 800 includes a first container 920a, a second container 920b, a third container 920c, and a fourth container 920d. In other examples, the rigid storage container 800 includes more or fewer containers than four. Each of the containers 920a, 920b, 920c, and 920d are substantially identical to the container 920. Container 920 is a blister pack having a tray 922 and a gas permeable film 924 enclosing the container 920. Contained within the container 920 is a prefilled medicament delivery device 926. In some examples, to access the prefilled medicament delivery device 926, the film 924 is peeled away from the tray 922. Alternatively, the prefilled medicament delivery device 926 can be pushed through the film 924 through the tray 922. In some examples, the prefilled medicament delivery device 926 is a prefilled syringe and the container additionally includes a syringe plunger 928. Each of the containers 920a, 920b, 920c, 920d container substantially identical contents.

Figure 10:
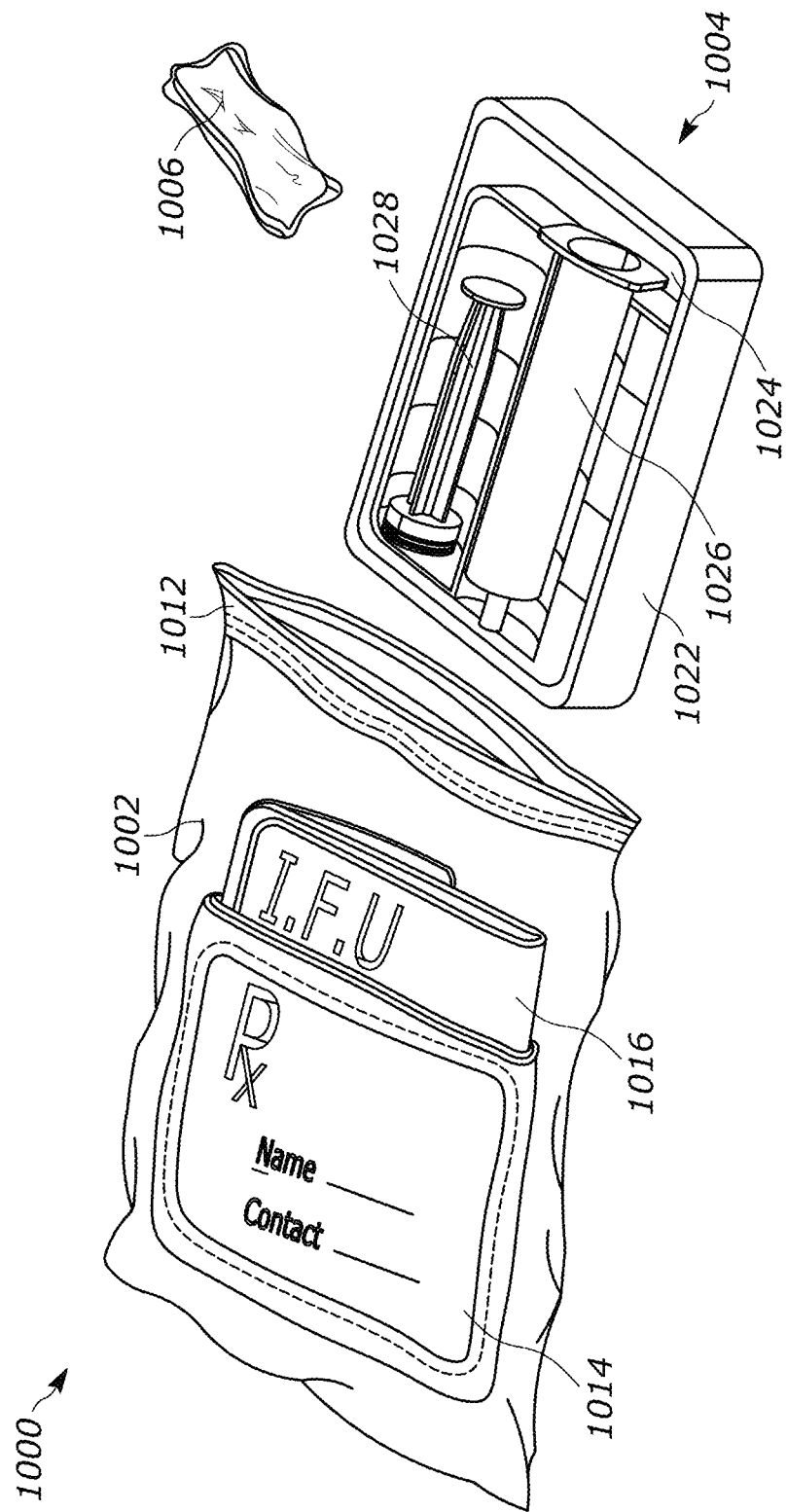
FIG. 10 is a perspective view of a container for storing one container having a medicament delivery device in accordance with the present disclosure.

FIG. 10 is a perspective view of prescription packaging 1000 including a container 1002 for storing one container 1004 and an absorbent 1006. The container 1002 of the prescription packaging 1000 is sealable with a seal 1012. In some examples, the container 1002 is a gas impermeable bag and the seal 1012 is resealable. The container 1002 additionally includes a label 1014 and instructions for use 1016 (IFU). The container 1002 can include the absorbent 1006, similar to the absorbent 206 and the absorbent 916. As a result, when the container 1002 is sealed, the absorbent 1006 maintains a desired relative humidity within the container 1002.

The prescription packaging additionally includes the container 1004 and is substantially similar to the container 920 of FIG. 9. The container 1004 includes a tray 1022 and a film 1024 to seal the container 1004. The container 1004 additionally includes the prefilled medicament delivery device 1026. In some examples, the prefilled medicament delivery device 1026 is a prefilled syringe and the container 1004 additionally includes a plunger 1028 to actuate the prefilled syringe. In some examples, the film 1024 is a gas permeable film that allows moisture to pass through the film 1024. In other examples, the film 1024 is not gas permeable and moisture cannot pass through the film 1024. In such examples, the absorbent 1006 is disposed within the container 1004.

Figure 11A:
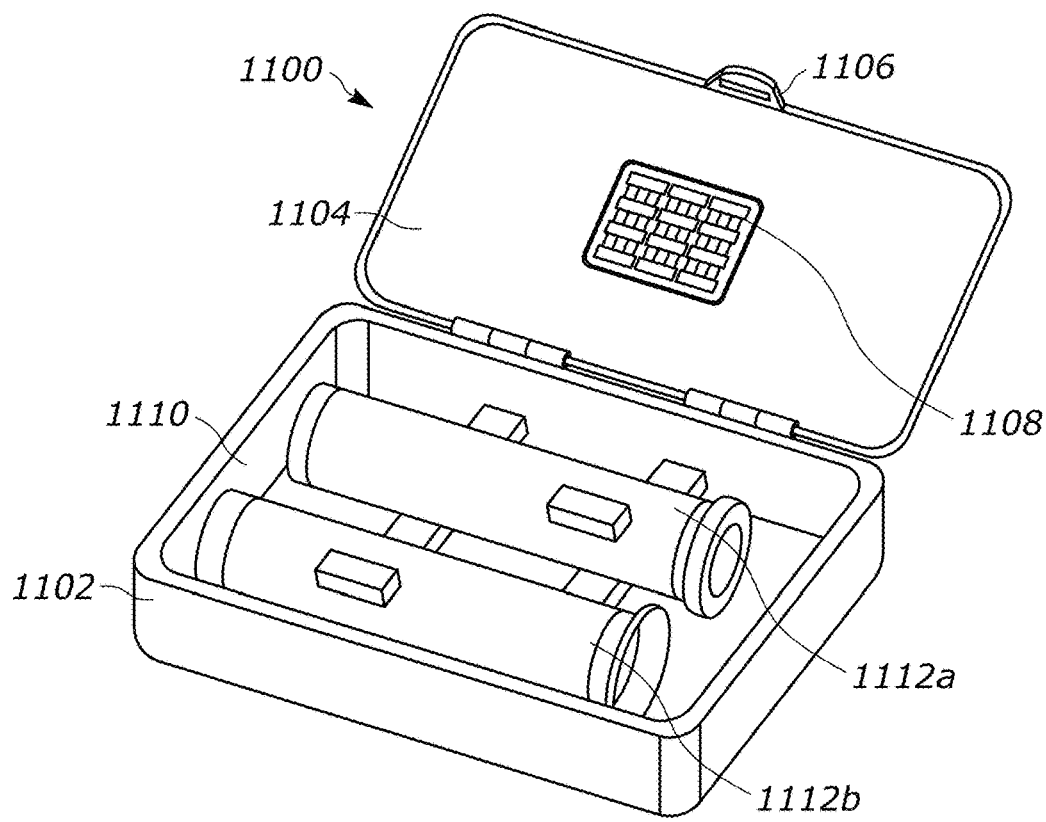
FIG. 11a is a perspective view of a rigid, travel container in an open state for storing at least one medicament delivery device in accordance with the present disclosure.

FIG. 11a is a perspective view of a rigid, travel container 1100 in an open state for storing at least one medicament delivery device. The travel container 1100 includes a bottom container 1102 and a lid 1104. The lid 1104 includes a latch 1106 to close the travel container 1100. The travel container 1100 is designed to store an absorbent carrier 1108 and at least prefilled medicament delivery device. As shown in FIG. 11a, the travel container 1100 includes a washable foam insert 1110 configured to receive a first prefilled medicament delivery device 1112a and a second prefilled medicament delivery device 1112b. In other examples, the travel container 1100 is designed to container more or fewer prefilled medicament delivery devices.

The travel container 1100 is designed to store and transport medicament delivery devices for short or long term travel. Accordingly, the travel container 1100 is designed to maintain a humid environment within the travel container for extended periods of time (e.g., days, weeks, months). As a result, the travel container creates a sealed environment and the absorbent carrier 1108 includes an absorbent to maintain humidity within the travel container when sealed. The absorbent carrier 1108 is similar to the absorbent carrier 910 of FIG. 9. For example, the absorbent carrier 1108 can be opened and rehydrated by a patient or other end user. Additionally, the absorbent carrier 1108 preferably includes antimicrobial properties to maintain sterility of the travel container 1100.

Figure 11B:
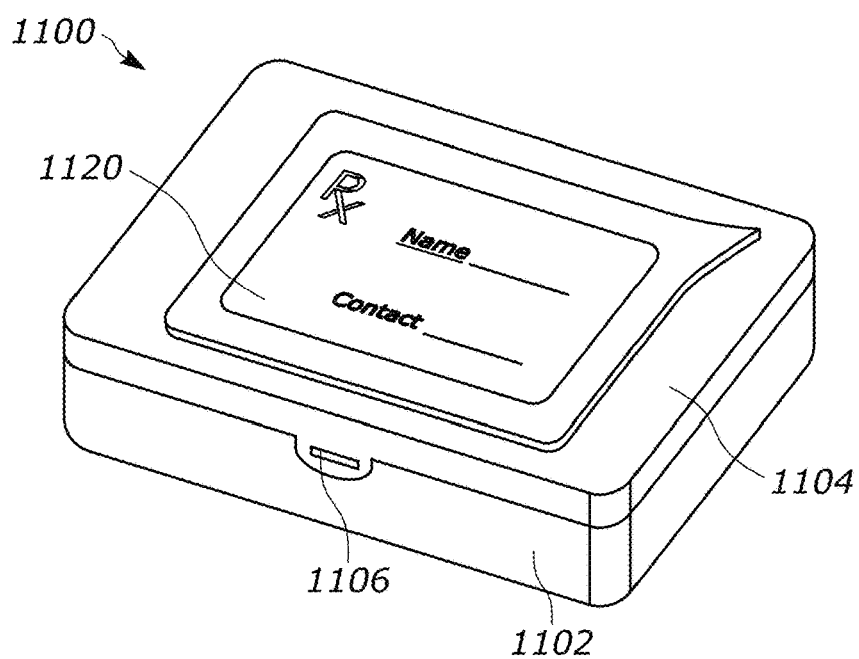
FIG. 11b is a perspective view of a rigid, travel container in a closed state for storing at least one medicament delivery device.

FIG. 11b is a perspective view of the rigid, travel container 1100 in a closed state for storing at least one medicament delivery device. The travel container 1100 includes a prescription label 1120. The prescription label 1120 is substantially similar to prescription label 1014. As shown in FIG. 11b, the latch 1106 can be used to both seal the container 1100 and also, when pulled, can open the container 1100. The rigid, travel container 1100 is designed to be small and sleek, for convenience during packing and short term travel storage.

While the apparatus and methods of the present disclosure have been described in connection with various embodiments, it will be understood that the apparatus and methods of the present disclosure are capable of further modifications. This application is intended to cover any variations, uses, or adaptations of the apparatus and methods following, in general, the principles of the present disclosure, and including such departures from the present disclosure as, within the known and customary practice within the art to which the disclosure pertains.

Furthermore, it is noted that the construction and arrangement of the disclosed long-term medicament storage apparatus, and their various components and assemblies, as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure.

It will be appreciated that the systems and approaches described herein may be used for the storage and transport of drugs in various states, such as but not limited to drug products which have undergone completion of mixing and/or other finishing steps, drug substances which are intended to be mixed and/or finished after shipping, components or ingredients to be used in a drug, or other drug-related states or components.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDE-NYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); Ova-Rex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim®

(MDX-1303, anti-*B. anthracis* protective antigen mAb); ABthrax™ Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) molecules such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF a monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl) ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a $KRAS^{G12C}$ small molecule inhibitor, or another product containing a $KRAS^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)×anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1 (PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed:

1. An apparatus for storing a medicament delivery device, the apparatus comprising:
   a container defining a storage cavity having an opening;
   a syringe pre-filled with medicament and disposed in the storage cavity;
   an absorbent disposed in the storage cavity, the absorbent at least partially hydrated with a liquid solution; and
   a seal member at least selectively connected with the storage cavity to form a seal that is at least substantially gas impermeable.

2. The apparatus of claim 1, wherein the cavity of the container and its contents are sterile.

3. The apparatus of claim 1, further comprising a gas permeable seal member disposed on the container over at least part of the opening enclosing at least part of the cavity containing the syringe, the gas permeable seal member disposed between the seal member and the container.

4. The apparatus of claim 3, wherein the cavity comprises a first sub-cavity and a second sub-cavity separated by a container wall, the first sub-cavity containing the syringe and the second sub-cavity containing the absorbent.

5. The apparatus of claim 4, wherein the gas-permeable seal member is disposed over the first sub-cavity but not the second sub-cavity, and the seal member is disposed over the first and second sub-cavities.

6. The apparatus of claim 1, wherein the absorbent is at least partially hydrated with a water solution.

7. The apparatus of claim 1, wherein the seal member is a sealed gas-impermeable bag in which the container, the syringe, and the absorbent are disposed.

8. A method of packaging a medicament delivery device for storage, the method comprising:
providing a container defining a storage cavity and an opening;
disposing a syringe pre-filled with a medicament in the storage cavity of the container;
disposing an absorbent in the storage cavity of the container, the absorbent being at least partially hydrated with a liquid solution; and
sealing the storage cavity of the container with a seal member by at least selectively connecting the seal member with cavity to form a seal that is at least substantially gas impermeable.

9. The method of claim 8, wherein sealing the storage cavity of the container comprises sealing the seal member to the container adjacent to the opening to enclose the storage cavity.

10. The method of claim 8, further comprising sterilizing the storage cavity and the syringe prior to sealing the storage cavity of the container with the seal member.

11. The method of claim 10, wherein sterilizing the storage cavity and the syringe comprises exposing the storage cavity and the syringe to a vapor phase hydrogen peroxide (VPHP) sterilizing process.

12. The method of claim 10, further comprising sealing at least part of the storage cavity containing the syringe with a gas-permeable seal member prior to sealing the storage cavity of the container with the seal member.

13. The method of claim 8, wherein sealing the storage cavity of the container comprises sealing the container in a sealed gas-impermeable bag.

14. The method of claim 8, wherein disposing the syringe in the storage cavity of the container comprises disposing the syringe in a first sub-cavity of the container, and disposing the absorbent in the storage cavity comprises disposing the absorbent in a second sub-cavity of the container, the first and second sub-cavities separated by a container wall.

15. The method of claim 8, further comprising hydrating the absorbent in a water solution for a predetermined period of time prior to disposing the absorbent in the cavity.

* * * * *